United States Patent
Chung et al.

(10) Patent No.: US 7,060,286 B2
(45) Date of Patent: Jun. 13, 2006

(54) **EXTERNAL PREPARATION FOR SKIN CONTAINING OLEAGINOUS SUBSTANCES EXTRACTED FROM *GANODERMA LUCIDUM***

(75) Inventors: Chee-Keung Chung, Room 2018, Argyle Centre, 688 Nathan Road, Mongkok, Kowloon (HK); Siu-Kan Tong, Kowloon (HK)

(73) Assignee: Chee-Keung Chung, Kowloon (HK)

( * ) Notice: Subject to any disclaimer, the term of this patent is extended or adjusted under 35 U.S.C. 154(b) by 0 days.

(21) Appl. No.: 10/777,652

(22) Filed: Feb. 13, 2004

(65) Prior Publication Data

US 2005/0180988 A1 Aug. 18, 2005

(51) Int. Cl.
- *A01N 63/00* (2006.01)
- *A01N 63/04* (2006.01)
- *A01N 65/00* (2006.01)
- *C12N 1/14* (2006.01)
- *C12N 1/16* (2006.01)

(52) U.S. Cl. .............. 424/401; 424/93.5; 424/195.15; 424/195.16; 435/171; 435/254.1; 435/911

(58) Field of Classification Search ............ 424/195.15
See application file for complete search history.

(56) References Cited

U.S. PATENT DOCUMENTS

| | | | |
|---|---|---|---|
| 4,675,198 A | 6/1987 | Sevenants | |
| 5,017,397 A | 5/1991 | Nguyen et al. | |
| 6,111,108 A | 8/2000 | Lopez-Avila et al. | |
| 6,251,877 B1 | 6/2001 | Park et al. | |
| 6,316,002 B1 | 11/2001 | Liu et al. | |
| 6,323,246 B1 | 11/2001 | Nakama et al. | |
| 6,348,201 B1 | 2/2002 | Murata et al. | |
| 6,440,420 B1 | 8/2002 | Liu et al. | |
| 6,468,542 B1 | 10/2002 | Liu et al. | |
| 6,514,744 B1 | 2/2003 | Murata et al. | |
| 2003/0095981 A1* | 5/2003 | Wong et al. ............ | 424/195.15 |

OTHER PUBLICATIONS

Wasser, Solomon P. et al.; Therapeutic Effects of Substances Occurring in Higher *Basidiomycetes* Mushrooms: A Modern Perspective; Critical Reviews in Immunology, 1999, vol. 19, p. 65-96.

Lin, Lee-Juian et al.; Separation of oxygenated triterpenoids from *Ganoderma lucidum* by high-performance liquid chromatography; Journal of Chromatography, 1987, vol. 410, p. 195-200.

El-Mekkawy, Sahar et al.; Anti-HIV-1 and Anti-HIV-1-Protease Substances from *Ganoderma lucidum*; Phytochemistry, 1998, vol. 49, No. 6, p. 1651-1657.

O'Neil, Carol E. et al.; Basidiospore Extracts: Evidence for Common Antigenic/Allergenic Determinants; Int. Archs Allergy appl. Immun., 1988, vol. 85, p. 161-166.

Kim, Kug Chan et al.; *Ganoderma lucidum* extract protects DNA from strand breakage caused by hydroxly radical and UV irradiation; International Journal of Molecular Medicine, 1999, vol. 4, p. 273-277.

Min, Byung-Sun et al.; Triterpenes from the Spores of *Ganoderma lucidum* and Their Inhibitory Activity against HIV-1 Protease; Chem Pharm Bull, 1998, vol. 46(10), p. 1607-1612.

Kino et al.; An immunomodulating protein, Ling Zhi-8 (LZ-8) prevents insulitis in non-obese diabetic mice; Diabetologia, 1990, vol. 33, p. 713-718.

Gengtao, Liu et al.; Some Pharamacological Actions of the Spores of *Ganoderma lucidum* and the Mycelium of *Ganoderma capense* (Lloyd) Teng Cultivated by Submerged Fermentation; Chinese Medical Journal, 1979, vol. 92(7), p. 496-500.

\* cited by examiner

*Primary Examiner*—David M. Naff
*Assistant Examiner*—Deborah K. Ware
(74) *Attorney, Agent, or Firm*—Fei-Fei Chao; Bingham McCutchen LLP

(57) ABSTRACT

The present invention provides an external preparation for skin which contains, as a major ingredient, oleaginous substances extracted from sporoderm-broken spores from *Ganoderma lucidum*. The spores are preferably being treated with germination activation. The oleaginous substances are preferred to be extracted by a supercritical fluid-carbon dioxide ($SCF-CO_2$) method. The oleaginous substances prepared by $SCF-CO_2$ is transparent and odorless. They also demonstrates effects on skin smoothening, wrinkles reduction, aging defiance, inflammation lessening, pigmentation lightening, and irritation alleviation. The external preparation can be a cosmetic or a therapeutic composition.

11 Claims, No Drawings

EXTERNAL PREPARATION FOR SKIN CONTAINING OLEAGINOUS SUBSTANCES EXTRACTED FROM *GANODERMA LUCIDUM*

FIELD OF THE INVENTION

The present invention relates to an external preparation for skin and methods for using the same. The external preparation contains oleaginous substances ("*Ganoderma* spore lipids") which are extracted from sporoderm-broken spores of *Ganoderma lucidum*. The spores of *Ganoderma lucidum* are preferred to be germination activated. The *Ganoderma* spore lipids are preferred to be extracted by a supercritical fluid-$CO_2$ method. The *Ganoderma* spore lipids are transparent and odorless and have the effects of smoothening skin, reducing wrinkles, defying aging, lessening inflammation, whitening pigmentation, and alleviating skin irritation. The external preparation is preferred to be a cosmetic or a topical formulation.

BACKGROUND OF THE INVENTION

The skin has a protection function against the surrounding environment such as change of temperature or humidity, ultraviolet, and/or pollution materials. The normal function of the skin may be depressed by the excessive physical or chemical stimulation and stresses, or nutrient deficiency, causing skin-aging and/or skin-damage.

The external preparations for skin, such as cosmetics or topical formulations, are designed to maintain the skin in a beautiful and healthy state. There are a variety of cosmetics and/or topical formulations in the market, most of them are in the form of lotions, creams, detergents, dispersion solutions, or ointments. These skin preparations generally contain ingredients which may or may not have any dermatological effect on the skin. For example, to maintain the skin in a smooth, moisturizing condition, humectants, such as glycerin, sorbitol, propylene glycol, polysaccharide, and the like, are generally used in the cosmetics or topical formulations. None of these ingredients have any dermatological effect.

Also, for lightening or whitening the spots and freckles on the skin, which are generally formed due to abnormal melanine deposits on the skin, a regional application of ointment, cream or lotion containing kojic acid, vitamin C/ascorbic acid, glutathione, or cysteine can be useful. The use of hydroquinone and derivatives thereof, which are known as melanine generation inhibitors, are also commonly known for the purpose of bleaching erythema dyschromium perstans. Most of these ingredients, however, exhibit dermatological effect on inhibiting melanine formation.

In addition, vitamin A, soybean extract, and/or seaweed extract, which have been used in the external preparation for skin to provide an anti-aging effect, to improve wrinkle, and restore skin damage due to ultraviolet rays exposure, have exhibited both cosmetic and dermatological effect on skin.

However, the shortcomings of these compounds are that most of them are synthetic in nature and serve only narrow function, which not only may cause allergic reaction on skin but also may not be effective for skin conditions such as inflammation, wounds, and/or skin irritation. Thus, finding an ingredient that does not cause allergic reaction on skin but has multiple functions will be of great value to the dermatological and beauty field.

*Ganoderma* (*Ganoderma lucidum* Leyss ex Fr. Karst) is a polyporous fungus. It belongs to the class of *Basidiomycetes*, the family of *Polypolaceae*, and the genus of *Ganoderma*. In Chinese folklore, *Ganoderma* has been regarded as a panacea, which is probably due to certain efficacy of *Ganoderma* in treating many diseases. Some of the known medicinal or therapeutic effects of *Ganoderma* include treating patients with chronic bronchitis, chronic viral hepatitis, coronary heart disease, granulocytopenia, chronic Keshan disease, neurasthenia, progressive muscular dystrophy, atrophic myotonia and certain neurological diseases (See e.g., Liu et al., Chinese Medical Journal, 92:496–500 (1979)). There are also reports on *Ganoderma* as anti-HIV agent (See e.g., El-Mekkawy et al., Phytochemistry, 49: 1651–1657 (1998); Min et al., Chem. Pharm. Bull, 46: 1607–1612 (1998)), or for having anti-tumor, cardiovascular, antiviral, antibacterial, antiparasitic, and immune modulating activities (See e.g., Wasser et al., Critical Review in Immunology, 19:65–96 (1999)).

There are two major types of compounds found in *Ganoderma* which have been shown to be associated with the medicinal or therapeutic effects of *Ganoderma*. They are the polysaccharide compounds and the terpenoids. The polysaccharide compounds are primarily water-soluble. The terpenoids are oleaginous substances and are generally insoluble in water.

The polysaccharide compounds isolated from *Ganoderma* include heteroβ-glucans and their protein complexes (such as xyloglucans and acidic β-glucan-containing uronic acid, dietary fibers, lectins). The polysaccharides found in *Ganoderma* have been reported to possess anti-tumor and immune modulating effects (See Wasser et al., supra).

The *Ganoderma* terpenoids contain a lanostane skeleton. They are classified into several groups based on their carbon numbers and state of oxidation (Komoda et al., Chem. Pharm. Bull., 33:4829–4835 (1985)). These *Ganoderma* terpenoids include lanostanine-type triterpenoids (e.g., ganoderic acids A, B, $C_1$, $C_2$, $D_1$, $D_2$, $E_1$, $E_2$, F, G, H, I, J, $K_1$, $K_2$, L, Ma, Mb, Mc, Md, Me, Mf, Mg, Mi, Mj, Mk, Mn, N, O, P, Q, S, T, U, V, W, X, Y, and Z), 7-O-methyl-ganoderic acid O, trideacetyl ganoderic acid T, ganoderenic acids A, B, C, D, E, F, G, H, I, ganolucidic acids A, B, C, D, and E, lucidenic acids A, B, C, $D_1$, $D_2$, $E_1$, $E_2$, F, G, H, I, J, K, L, M, ganoderiol type 1 (A, B, F) and type 2 (C, D, E, F, G, H, and I), ganoderal A and B, epoxyganoderiol A, B, C, lucidone A, B, C, furanoganoderic acid, and other terpenoid components. *Ganoderma* terpenoids (e.g., ganoderic acids R, T, U-Z) have been reported to inhibit growth of hepatoma cells in vitro (See Toth et al., Tetrahedron Lett., 24:1081–1084 (1983)). The *Ganoderma* terpenoids are hereinafter referred to as "*Ganoderma* spore lipids" to reflect the water-insoluble, oleaginous characteristics of the compounds.

There have been reports on methods for breaking the epispores of *Ganoderma* spores. For example, Japanese Patent No. JP52041208 discloses an extraction method for breaking *Ganoderma* spores using mechanical force. Chinese Patent No. CN1134306 teaches a method for breaking the sporoderm of the *Ganoderma* spores by soaking the spores in water, followed by microwave-heating. Chinese Patent No. CN1165032 teaches a method for breaking the cell wall of *Ganoderma lucidum* spores by digesting the spores with skin-dissolving enzymes such as lysozyme, snail enzyme, cellulase, or hemicellulase, followed by ultrasonic breakage of the cell walls at 20–50° C. More recently, the inventor of this invention has disclosed a germination-activation method for treating the *Ganoderma* spores prior to the breaking of the epispores. See U.S. Pat. Nos. 6,316, 002 and 6,468,542, which are herein incorporated by reference. The germination-activation procedure synchronizes the growth of and induces the maximum production of biological substances within of the *Ganoderma* spores. The germination-activated sporoderm-broken *Ganoderma* spores have demonstrated therapeutic effects on various diseases.

The biological substances in the *Ganoderma* spores contain, inter alia, active genes and promoters, active enzymes, sterols, cytokines, interferons, lactone A, *ganoderma* acid A, triterpenes, polysaccharides, vitamins, superoxide dismutases (SOD), glycoproteins, etc. These biological substances demonstrated superb medicinal effects, particularly on stimulating and modulating the nervous system and the immune system. These biological substances also demonstrated therapeutic effects on liver cancer and HBV infection. Additionally, when the *Ganoderma* spores were given to animals, the sporoderm-unbroken spores had an anti-tumor rate of 23.2%, which was substantially lower than the sporoderm-broken spores, which had an anti-tumor rate of 86.1%.

There have been reports on isolation or separation of the oleaginous substances (e.g., the terpenoids) from *Ganoderma*, most involving the use of organic solvents. For example, Min et al., *Chem. Pharm. Bull.*, supra, disclose the isolation of lanostane-type triterpenes using column chromatography of a $CHCl_3$-soluble fraction of the methanol extract of the *Ganoderma* spores. Lin et al., *J. Chromatography*, 410: 195–200 (1987) disclose the separation of oxygenated triterpenoids from *Ganoderma lucidum* by high-performance liquid chromatography of a methanolic extract of *Ganoderma lucidum*. These methods are unsatisfactory due to complex extraction procedures and low yield of the oleaginous substances.

Recently, a method for extracting oleaginous substances from sporoderm-broken *Ganoderma* spores has been disclosed also by the inventor of this invention in U.S. Pat. No. 6,440,420, which is herein incorporated by reference. The method includes (1) breaking up the sporoderm of the germination-activated *Ganoderma* spores by a mechanical means; and (2) extracting the *Ganoderma* spore lipids from the sporoderm-broken germination-activated *Ganoderma* spores by a supercritical fluid carbon dioxide ($SCF-CO_2$) extraction method. This method produces high yield of *Ganoderma* spore lipids from *Ganoderma* (i.e., the yield of the *Ganoderma* spore lipids is about 37% by weight of the entire biological substances released from *Ganoderma*). The *Ganoderma* spore lipids extracted by this method is transparent and odorless.

In the present invention to be described in the following sections, an external preparation for skin comprising the *Ganoderma* spore lipids extracted from sporoderm-broken *Ganoderma* spores using the $SCF-CO_2$ method is provided. The *Ganoderma* spore lipids demonstrate multiple functions in smoothening skin, reducing wrinkles, defying aging, lessening inflammation, whitening pigmentation, and alleviating skin irritation, thus making it an ideal ingredient to be used in both the cosmetic and the dermatological field.

SUMMARY OF THE INVENTION

The present invention provides an external preparation for skin, which is preferably a cosmetic or a topical formulation having dermatological effect on skin. The external preparation contains oleaginous substances (hereinafter "*Ganoderma* spore lipids") extracted from the spores of *Ganoderma lucidum*. The *Ganoderma* spores are preferably sporoderm-broken, and most favorably, germination-activated sporoderm-broken. The sporoderm of the *Ganoderma* spores are preferably broken by a mechanical means or by enzyme digestion. The external preparation for skin further comprises a carrier.

The *Ganoderma* spore lipids used in the external preparation are transparent and odorless. It is extracted from either the sporoderm-broken or the germination-activated sporoderm-broken *Ganoderma* spores by a supercritical fluid-carbon dioxide ($SCF-CO_2$) extraction method. The preferred temperature used in the $SCF-CO_2$ extraction is at about 32° C. to 45° C. Higher temperature will result in a darker and less transparent *Ganoderma* spore lipids.

The *Ganoderma* spore lipids demonstrate beautifying and dermatological effects on smoothening, reducing wrinkles, defying aging (i.e., repairing damaged skin and making the skin looked younger and more elastic), and reducing pigmentation (i.e., whitening or bleaching the spots and freckles) of the skin, especially on the facial skin (including the eyelid area).

In addition, the *Ganoderma* spore lipids have dermatological effects in lessening skin inflammation (e.g., swollen skin caused by injury) or alleviating skin irriation, (e.g., itching or pain due to herpes zoster infection or psoriasis).

The beautifying and dermatological effects of the *Ganoderma* spore lipids on the skin are more apparent if the individual who has topically used the *Ganoderma* spore lipids also concurrently takes the *Ganoderma* spore lipids capsule orally on a daily basis. The daily effective dosage of *Ganoderma* spore lipids is 1–2 capsule per day (containing 150 mg of *Ganoderma* spore lipids per capsule).

The effect of *Ganoderma* spore lipids on the appearance of skin is also synergistically improved if it is coupled with concurrent oral uptake of the germination-activated sporoderm-broken *Ganoderma* spores. The germination-activated sporoderm-broken *Ganoderma* spores are preferably to be prepared by germinating the *Ganoderma* spores in a soaking solution containing 5% of mycelia of *Ganoderma*, 5% of mycelia of Cordyceps, 5% of malt extract, and 5% coconut juice in water. The preferred soaking condition for germination is at about 25° C. for about 8 hours. The germinated *Ganoderma* spores are then put in a cultural box and activated for about 12 hours at about 25° C. and relative humidity of about 80%.

The recommended dosage of the germination-activated sporoderm-broken *Ganoderma* spores is 2–4 capsules per day (300 mg per capsule). The preferred germination-activated sporoderm-broken *Ganoderma* spores have about 95%–100% sporoderm-broken rate.

The present invention also provides methods for smoothening skin, reducing wrinkles on skin, defying aging of skin, reducing pigmentation deposited on skin, lessening skin inflammation, and alleviating skin irritation, by applying the *Ganoderma* spore lipids-containing external preparation to the area of the skin of a human which requires such treatment.

DETAILED DESCRIPTION OF THE INVENTION

*Ganoderma* spores are tiny mist-like brown oval-shaped spores of 6~7 µm×10~12 µm in sizes which are released at the pelius of mature *Ganoderma lucidum*. These spores contain the entire genetic materials and biological substances of *Ganoderma*. However, the wild *Ganoderma* spores are difficult to collect, particularly due to their short release period and low germination rate under unfavorable environmental conditions. Therefore, although it is known that the *Ganoderma* spores are of greater pharmaceutical values than the fruiting bodies of *Ganoderma*, due to difficulties associated with the collection of the *Ganoderma* spores, most of the studies on *Ganoderma* are conducted using the fruiting bodies of *Ganoderma*.

The biological substances within the *Ganoderma* spores which give rise to the therapeutic effects of *Ganoderma* are stored within the double-layered epispores of *Ganoderma lucidum*. However, these epispores have compact structure, which are extremely rigid and resilient. Therefore, it is very difficult to break-open the epispore layers of the *Ganoderma* spores and release the biological substances therein using conventional extraction methods.

The present invention provides an external preparation for skin which contains oleaginous substances ("*Ganoderma* spore lipids") extracted from sporoderm-broken *Ganoderma* spores.

The sporoderm-broken *Ganoderma* spores can be prepared by the following process:

1. Collection of *Ganoderma* Spores: Mature and plump *Ganoderma* spores are collected at the appropriate release time from *Ganoderma lucidum* cultured on log. It is advantageous to culture *Ganoderma* on log, because the spores thus produced are fresher and more nutritious and the penetration/breaking rate for the epispores is much higher.

2. Penetration/Breakage of the Epispores: After the *Ganoderma* spores are collected, the spores are broken by a mechanical means. Examples of the mechanical means used to break the spores include micronization, roll-pressing, or scissor-cut/grinding, microstream-impact crushing, ultra-high-speed airstream impact crushing, ultra-high pressure microstream crushing, ultra-low temperature crushing etc.

Before breaking the epispores, it is optional to treat the spores with enzymes such as chitinase and cellulase to soften the cell walls of the epispores. The enzyme-treated spores can be separated from the reaction mixture by centrifugation at about 3,000~30,000 rpm or ultra-filtration using a filter with about 10,000 molecular weight cut-off.

Prior to the breaking of the epispores, it is preferred to treat the *Ganoderma* spores with a germination procedure followed by an activation step as follows:

a). Induction of *Ganoderma* Spores Germination: The selected spores are soaked in a nutritional solution which can be distilled water, a saline solution, a solution which has been immersed with the fruiting bodies of *Ganoderma* or the mycelia of *Ganoderma*. The purpose of soaking the spores in the nutritional solution is to enable and accelerate the germination of the spores. Examples of the nutritional solution include 0.5~25% by weight of the immersion solution of the *Ganoderma* fruiting bodies or mycelia, 0.1~0.5% by weight of the biotin solution, etc. The nutritional solution is about 0.01~5 times of the weight of the *Ganoderma* spores. The soaking time is about 10 minutes~8 hours. The temperature is about 16~43° C.

For a maximal germination in a large scale preparation, it is preferred that the *Ganoderma* spores are soaked in a soaking solution (in water) containing 5% of mycelia of *Ganoderma*, 5% of mycelia of Cordyceps, 5% malt extract, and 5% coconut juice. The ratio between the *Ganoderma* spores and the soaking solution is preferred to be about 1:2 (wt:vol.). It is also preferable to include 5% of animal albumin in the soaking solution. The soaking period is preferably about 8 hours and at a temperature of 25° C.

b). Activation of the Germinated *Ganoderma* Spores: To activate the germinated *Ganoderma* spores, the soaked spores are removed from the nutritional solution and excess solution is allowed to drip. The soaked spores are then placed in a well-ventilated culture box which is kept in constant temperature and humidity. The relative humidity in the culture box is maintained at about 60~98%. The temperature of the culture box is maintained at about 16~48° C.

To reach a maximum activation rate, the germinated *Ganoderma* spores is preferred to be put in the cultural box at about 25° C. for about 12 hours and at about 80% relative humidity.

The *Ganoderma* spore lipids are then extracted from the sporoderm-broken by a SCF-$CO_2$ method as follows:

Extraction of *Ganoderma* Spore Lipids with SCF-$CO_2$: The extraction of the *Ganoderma* spore lipids from the sporoderm-broken spores is conducted in a SCF-$CO_2$ extracting apparatus, which includes a $CO_2$ source, a compressor, a heat exchanger, a pressure regulator, and a pressure vessel. Alternatively, any conventional supercritical fluid extraction equipment which contains an extractor (i.e., the pressure vessel) and a separator should also be suitable for the extraction. To operate, the sporoderm-broken spores are placed in the pressure vessel. The carbon dioxide is flowed through the compressor and heat exchanger to achieve greater than supercritical temperature and pressure, and then flowed through the spores in the pressure vessel. The SCF is then removed from the pressure vessel and depressurized to evaporate the carbon dioxide. The supercritical pressure used in the present method is about 5~60 MPa. The supercritical temperature is about 32~85° C. Preferably, the supercritical temperature is about 32~45° C. to yield a transparent and odorless extract. The *Ganoderma* spore lipids produced in a higher temperature are darker in color and less transparent. The flow volume rate of $CO_2$ is about 5~80 kg/h. The extraction time is about 0.5~6 hours.

It is optional to add a sovent to the spores between initiating the SCF-$CO_2$ extraction. Examples of the solvent include water and/or 85~100% of ethanol. The ratio of the solvent to the spores is about 2~200% (v/w). When the solvent is added to the spores, the *Ganoderma* spore lipids can be separated from the rest of the spores by centrifugation at about 3,000~30,000 rpm.

The present invention provides an external preparation for skin, which is either a cosmetic or a topical formulation having dermatological effect on skin. The external preparation contains the *Ganoderma* spore lipids and optionally a carrier. The preferred carrier includes, but is not limited to, oils, Vitamins and alcohols etc.

Examples of the oils include liquid fats and oils such as avocado oil, camellia oil, turtle oil, macadamia nut oil, corn oil, mink oil, olive oil, rapeseed oil, yolk oil, sesame oil, pearshic oil, wheat germ oil, sasanqua oil, castor oil, linseed oil, safflower oil, cotton seed oil, evening primrose oil, perilla oil, soybean oil, peanut oil, tea seed oil, kaya oil, rice bran oil, Chinese paulownia oil, Japanese paulownia oil, jojoba oil, germ oil, triglycerin, glycerin trioctanoate, glycerin triisopalmitate and the like; solid fats and oils such as cacao butter, coconut oil, horseflesh tallow, hydrogenated coconut oil, palm oil, beef tallow, ram tallow, hardened beef tallow, palm kernel oil, lard tallow, beef bone tallow, Japan wax kernel oil, hardened oil, beef leg tallow, Japan wax, hydrogenated castor oil and the like; waxes such as beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hardened lanolin, shellac wax, POE lanolin alcohol ether, POE lanolin alcohol acetate, lanolin fatty acid polyethylene glycol, POE hydrogenated lanolin alcohol ether and the like; hydrocarbons such as liquid paraffin, ozocerite, squalene, pristane, paraffin, ceresine, squalane, vaseline, microcrystalline wax and the like; and synthetic esters such as isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearylate, ethyleneglycol di-2-ethylhexylate, dipentaerythritol fatty acid ester, N-alkylglycol monoisostearate, neopentylglycol dicapriate, diisostearyl malate, glycerin di-2-heptylundecanoate, trimethylolpropane tri-2-ethylhexylate, trimethylolpropane triisostearate, pentaerythritol tetra-2-ethylhexylate, glycerin tri-2-ethylhexylate, trimethylolpropane triisostearate, cetyl 2-ethylhexanote, 2-ethylhexyl palmitate, glycerin trimyristate, glyceride tri-2-heptylundecanoate, castor oil fatty acid methyl ester, oleic acid oil, cetostearyl alcohol, acetoglyceride, 2-heptylundecyl palmitate, diisopropyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succiniate, ethyl acetate, butyl acetate, amyl acetate, triethyl citrate and the like. Occasionally, polar oils such as 2-octyldodecanol and the like can also be included.

In addition to the above oily ingredients, a small amount of a silicone oil such as straight polysiloxane, dimethylpolysiloxane, methylphenylpolysiloxane, methylhydrogen-polysiloxane and the like may also be incorporated in the external preparation.

Examples of Vitamins include, but not are limited to, vitamin A and derivatives thereof, vitamin D and derivatives thereof, vitamin E and derivatives thereof, vitamin K and derivatives thereof and the like.

Optionally, sterols, natural and synthetic perfumes and the like may be incorporated.

The cosmetic or topical formulation include, without limitation, lotion, liniment, gel, emugel, cream, ointment or paste. Methods for making the cosmetic and/or topical formulation of the external preparations are well known to those of skill in the art. Also, in addition to the *Ganoderma* spore lipids, other topical ingredients that can be used in the cosmetic or topical formulation are in general those commonly used and generally recognized by person skilled in the art.

For example, the suitable ingredients that can be added to the *Ganoderma* spore lipids in a lotion or liniment include those suitable for application to the skin, such as alcohol or acetone, which can hasten drying and cooling of the solution on the skin. A moisturizer, such as glycerol, or an oil, such as castor oil or arachis oil, may also be included.

For the preparation of cream, ointments, or pastes, the *Ganoderma* spore lipids is generally mixed with a greasy or non-greasy base, with the aid of suitable machinery. The base may contain hydrocarbons. Examples of the hydrocarbons include, but are not limited to, hard, soft, or liquid paraffin, glycerol, beeswax, a metallic soap, a mucilage, an oil of natural origin (such as almond, corn, arachis, castor or olive oil), wool fat or its derivative, a fatty acid (such as stearic acid or oleic acid), or a combination thereof. The cosmetic or topical formulation may also contain a surface active agent, such as an anionic, cationic or non-ionic surfactant. Examples of the surfactants include, but are not limited to, sorbitan esters or polyoxyethylene derivatives thereof (such as polyoxyethylene fatty acid esters) and carboxypolymethylene derivatives thereof (such as carbopol). Suspending agents such as natural gums, cellulose derivatives inorganic materials such as silicaceous silicas, and other ingredients such as lanolin, may also be included. For ointment, polyethylene glycol 540, polyethylene glycol 3350, and propylene glycol may also be used to mixed with the *Ganoderma* spore lipids.

For the preparation of a gel or emugel, the cosmetic or topical formulation can include any gel forming agent commonly used in the gel formulations. Examples of gel forming agents are cellulose derivatives such as methyl cellulose, hydroxyethyl cellulose, and carboxymethyl cellulose; vinyl polymers such as polyvinyl alcohols, polyvinyl pyrrolidones; carboxypoly-methylene derivatives such as carbopol. Further gelling agents that can be used for the present invention are pectins and gums (such as gum arabic and tragacanth, alginates, carrageenates, agar and gelatin). The preferred gelling agent is carbopol. Furthermore, the gel or emugel formulation may contain auxiliary agents commonly used in the kind of formulations such as preservatives, antioxidants, stabilizers, colorants, and perfumes.

The external preparation for skin compositions may further contain additional ingredients, such as colorants, perfumes, and the like. Suitable cosmetically acceptable carriers and additional ingredients, for use herein, can be found in the CTFA Cosmetic Ingredient Dictionary ($3^{rd}$ ed., 1982) and the CTFA Cosmetic Ingredient Handbook, ($2^{nd}$ ed., 1992), both published by The Cosmetic, Toiletry & Fragrance Association, Inc., which references are incorporated herein by reference in their entirety.

The amount of the *Ganoderma* spore lipids in the cosmetic or topical formulation varies widely, depending upon the intended use of the external preparation, which ranges from 0.1% by weight to 100% by weight.

The external preparation for skin of the present invention can be applied to any body surface, i.e., any skin area of the body, including skin areas covered by hairs. Preferably, the external preparation for skin is applied to facial areas where the user wants to cosmetically improve the skin conditions, that is, to improve the appearance of the skin (e.g., make skin smoother, lighter in color, more elastic, less wrinkled, and/or fewer blemishes). The skin conditions in the areas to be treated may be aged, stressed, discolored, pigmented, irritated, wrinkled, damaged, injured, inflamed, with skin abnormality, and/or suffering from common skin diseases. Examples of skin diseases include, but are not limited to, herpes zoster and psoriasis. The skin area to be treated can also be normal (e.g., free from above listed condition).

The external preparation for skin of the present invention is safe for long-term use. The effective amount of the external preparation and frequency of application depend on the intended use of the external preparation, the severity of the skin conditions and the sizes of skin areas being treated. The user adjust the amount used based on his/her own conditions. In general, for normal skin (least severe skin condition), the user applies an amount of the external preparation lesser than that for pigmented/discolored skin areas, lesser than that for injured or diseased skin areas (most severe skin condition), e.g., skin wounds, herpes zoster, and psoriasis.

The external preparation for skin of the present invention can also be used concurrently with oral uptake of the *Ganoderma* spore lipids capsule (each capsule contains 150 mg of *Ganoderma* spore lipids) and/or the germination-activated sporoderm-broken *Ganoderma* spores, both manufactured and sold by Enhan Technology Holdings International Co., Ltd., in Kowloon, Hong Kong, under the trademark of "ENHANVOL®".

The following examples are illustrative, but not limiting the scope of the present invention. Reasonable variations, such as those occur to reasonable artisan, can be made herein without departing from the scope of the present invention.

EXAMPLES

The following case studies are based on direct application of the *Ganoderma* spore lipids extracted from germination-activated sporoderm-broken spores of *Ganoderma lucidum* by a SCF-CO$_2$ method. The *Ganoderma* spore lipids is contained in a soft capsule (each capsule contains 150 mg of the *Ganoderma* spore lipids), and manufactured and sold by Enhan Technology Holdings International Co., Ltd., in Kowloon, Hong Kong under the trademark of ENHANVOL® (G SPORE LIPID). The same company also manufactured and sold capsules of the germination-activated sporoderm-broken *Ganoderma* spores (each capsule contains 300 mg of spores), also under the trademark of ENHANVOL®.

Case 1: A 45-year-old male patient suffered from herpes zoster attack in 2003 with big vesicles on the left scalp extending to the upper neck. The patient applied *Ganoderma* spore lipids directly to the vesicles, which provided instant pain relief from the herpes flare up, the patient felt only the itchiness. The *Ganoderma* spore lipids also speeded up the recovery. The patient recovered from the herpes flare up within one week, which was much shorter than the standard period of time a textbook described for the duration of herpes flare up. This patient has been orally taking the *Ganoderma* spore lipids capsule daily since 2002 and the germination-activated sporoderm-broken *Ganoderma* spores since 2000.

Case 2: A 50-year-old female patient recently suffered from an accidental wound when, while opening a door, the door quickly rebounded. Her hand immediately became swollen and she suffered intense pain. The patient applied the *Ganoderma* spore. lipids to the affected area. Within one hour, the pain and the swelling had subsided. By the next day, the swelling was reduced by half and there was no further pain. The swelling had completely disappeared in a couple of days. This patient has never orally taken any germination-activated sporoderm-broken *Ganoderma* spores or *Ganoderma* spore lipids .

Case 3: A 35-year-old male patient had itchy skin at the forehead area recently. The patient applied the *Ganoderma* spore lipids to the affected area. The itchiness disappeared in an hour or so. The patient did not take any germination-activated sporoderm-broken *Ganoderma* spores or *Ganoderma* spore lipids.

Case 4: A 50-year-old healthy female applied the *Ganoderma* spore lipids to her facial skin as a cosmetic recently. Within two weeks after her application, she reported that her facial skin became much smoother. In addition, some of the wrinkles and spots/freckles on her face began to vanish. There was no adverse allergic reaction on her skin. She continued to use the *Ganoderma* spore lipids until today (twice a week). The individual in this case has never taken any germination-activated sporoderm-broken *Ganoderma* spores or *Ganoderma* spore lipids.

Case 5: A 48-year-old male patient had suffered from a long history of psoriasis. The patient took the *Ganoderma* spore lipids orally but experienced no relief for the itchiness. The patient recently applied the *Ganoderma* spore lipids directly to the affected area and received instant relief on inflammation. He also experienced less itchiness.

Case 6: A 45-year-old male patient took the germination-activated sporoderm-broken *Ganoderma* spores orally since 1999. The patient also began applying the *Ganoderma* spore lipids on his face three times a week since 2001. The patient noticed that his facial skin became smoother and the spots/freckles and wrinkles on his face became less apparent. The texture of the skin also became more elastic and youthful.

Case 7: A 43-year-old female took the germination-activated sporoderm-broken *Ganoderma* spores orally for relief of her constipation since 1999. The patient also had brown pigments all over her face, probably due to the accumulation of toxins caused by constipation. She began to apply the *Ganoderma* spore lipids four times a week since 2002. The patient recently reported that the brown pigments on her face had almost completely disappeared. Her skin texture also became much more elastic and the wrinkles on her face became less apparent.

Case 8: A 55-year-old female patient had subcutaneous lipid modules beneath her eyelids. The patient began to apply the *Ganoderma* spore lipids since September 2001. After applying the *Ganoderma* spore lipids, she noticed that the growth of the liquid nodules slowed down, and the liquid nodules began to reduce in size. In addition, her skin texture was much more elastic and the spots/freckles and wrinkles on her face became less apparent.

Case 9: A 51-year-old female patient took the germination-activated sporoderm-broken *Ganoderma* spores orally since late 1999 for her uterine fibroma and ovarian cyst. In mid-2000, her ultrasound test showed both the fibroma and the ovarian cyst had become smaller. She began to apply the *Ganoderma* spore lipids 3~4 times per week as a skin cosmetic in late 2001. The patient recently reported that the brown pigments on her face became less apparent and the wrinkles around her eyes were greatly reduced. Her skin texture also became more elastic and felt much smoother.

While the invention has been described by way of examples and in term of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. An external preparation for skin comprising:
    oleaginous substances extracted from germination-activated sporoderm-broken spores of *Ganoderma Lucidum* and a cosmetically acceptable carrier,
    wherein said external preparation is a skin cosmetic and wherein said skin cosmetic is applied to external skin of a human;
    wherein said oleaginous substances are extracted from said sporoderm-broken spores of *Ganoderma Lucidum* by a supercritical fluid-carbon dioxcide SCF-CO$_2$ extraction method; and
    wherein said skin cosmetic is capable of smoothening said external skin of said human.

2. The external preparation according to claim 1, wherein said oleaginous substances are transparent and odorless.

3. The external preparation according to claim 1, wherein said supercritical fluid-carbon dioxide (SCF-CO$_2$) extraction method is performed at a temperature of about 32° C. to 45° C.

4. The external preparation according to claim 1, wherein said skin cosmetic is further capable of reducing wrinkles from said external skin of said human.

5. The external preparation according to claim 1, wherein said skin cosmetic is further capable of defying aging of said external skin of said human.

6. The external preparation according to claim 1, wherein said skin cosmetic is further capable of reducing pigmentation of said external skin of said human.

7. An external preparation comprising:

oleaginous substances extracted from germination-activated sporoderm-broken spores of *Ganoderma Lucidum* and a cosmetically acceptable carrier, wherein said external preparation is a topical formulation having dermatological effect on external skin;

where in said topical formulation is applied to said external skin of a human;

wherein said oleaginous substances are extracted from said sporoderm-broken spores of *Ganoderma Lucidum* by a supercritical fluid-carbon dioxcide $SCF-CO_2$, extraction method; and wherein said topical formulation is capable of reducing inflammation of said external skin of said human.

8. The external preparation according to claim 7, wherein said inflammation is caused by skin injury.

9. The external preparation according to claim 7, wherein said topical formulation is capable of reducing skin irritation of said human.

10. The external preparation according to claim 9, wherein said skin irritation is caused by herpes zoster infection.

11. The external preparation according to claim 9, wherein said skin irritation is caused by psoriasis.

* * * * *